(12) United States Patent
Jongen

(10) Patent No.: US 9,289,624 B2
(45) Date of Patent: Mar. 22, 2016

(54) GANTRY COMPRISING BEAM ANALYSER FOR USE IN PARTICLE THERAPY

(75) Inventor: Yves Jongen, Louvain-la-Neuve (BE)

(73) Assignee: ION BEAM APLICATIONS, S.A., Louvain-la-Neuve (BE)

(*) Notice: Subject to any disclaimer, the term of this patent is extended or adjusted under 35 U.S.C. 154(b) by 0 days.

(21) Appl. No.: 13/502,946

(22) Filed: Apr. 19, 2012

(65) Prior Publication Data

US 2012/0280150 A1    Nov. 8, 2012

Related U.S. Application Data

(63) Continuation of application No. PCT/EP2010/065707, filed on Oct. 19, 2010.

(30) Foreign Application Priority Data

Oct. 23, 2009    (EP) .................................... 09173989

(51) Int. Cl.
| | |
|---|---|
| *H01J 3/26* | (2006.01) |
| *A61N 5/10* | (2006.01) |
| *G21K 1/093* | (2006.01) |
| *G21K 5/04* | (2006.01) |

(52) U.S. Cl.
CPC ................ *A61N 5/10* (2013.01); *A61N 5/1081* (2013.01); *G21K 1/093* (2013.01); *G21K 5/04* (2013.01); *A61N 2005/1087* (2013.01)

(58) Field of Classification Search
CPC ..... A61N 5/1077; A61N 5/1081; H05H 7/12; H05H 13/04; H01J 2237/0455; H01J 3/26; G21K 1/04; G21K 1/093

USPC .................................. 250/492.3; 378/65; 600/1
See application file for complete search history.

(56) References Cited

U.S. PATENT DOCUMENTS

| | | | |
|---|---|---|---|
| 6,433,336 B1 | 8/2002 | Jongen et al. | |
| 6,683,318 B1* | 1/2004 | Haberer et al. | 250/492.3 |
| 2004/0227104 A1* | 11/2004 | Matsuda et al. | 250/492.1 |
| 2008/0006776 A1 | 1/2008 | Furukawa | |
| 2008/0023644 A1* | 1/2008 | Pedroni | 250/400 |
| 2009/0020711 A1* | 1/2009 | Hansmann et al. | 250/492.3 |
| 2009/0289194 A1* | 11/2009 | Saito | 250/396 R |
| 2009/0321665 A1 | 12/2009 | Timmer et al. | |
| 2010/0127183 A1* | 5/2010 | Iseki et al. | 250/396 ML |
| 2014/0343346 A1* | 11/2014 | Yajima | A61N 5/1078 600/1 |

FOREIGN PATENT DOCUMENTS

| | | |
|---|---|---|
| DE | 102007032025 A1 | 12/2008 |
| WO | 2005102453 A1 | 11/2005 |

OTHER PUBLICATIONS

International Report on Patentability.
Blosser H et al. "Medical accelerator projects at Michigan State University", 19890320; 19890320-19890323, Mar. 20, 1989.

* cited by examiner

*Primary Examiner* — Jack Berman
*Assistant Examiner* — Kevin Chung
(74) *Attorney, Agent, or Firm* — Finnegan, Henderson, Farabow, Garrett & Dunner, LLP

(57) ABSTRACT

The present invention relates to a particle therapy apparatus used for radiation therapy. More particularly, this invention relates to a gantry for delivering particle beams which comprises means to analyse the incoming beam. Means are integrated into the gantry to limit the momentum spread of the beam and/or the emittance of the beam.

19 Claims, 6 Drawing Sheets

GANTRY COMPRISING BEAM ANALYSER FOR USE IN PARTICLE THERAPY

This application is a Continuation of PCT/EP2010/065707 filed Oct. 19, 2010, which in turn claims priority to European Patent Application No.: 09173989.6, filed on Oct. 23, 2009.

FIELD OF THE INVENTION

The present invention relates to a charged particle therapy apparatus used for radiation therapy. More particularly, this invention relates to a rotatable gantry designed for receiving a charged particle beam in a direction substantially along a rotation axis of the gantry, for transporting and for delivering said beam to a target to be treated.

STATE OF THE ART

Radiotherapy using charged particles (e.g. protons, carbon ions, . . . ) has proven to be a precise and conformal radiation therapy technique where a high dose to a target volume can be delivered while minimizing the dose to surrounding healthy tissues. In general, a particle therapy apparatus comprises an accelerator producing energetic charged particles, a beam transport system for guiding the particle beam to one or more treatment rooms and, for each treatment room, a particle beam delivery system. One can distinguish between two types of beam delivery systems, fixed beam delivery systems delivering the beam to the target from a fixed irradiation direction and rotating beam delivery systems capable of delivering beam to the target from multiple irradiation directions. Such a rotating beam delivery system is further named gantry. The target is generally positioned at a fixed position defined by the crossing of the rotation axis of the gantry and the central treatment beam axis. This crossing point is called isocenter and gantries of this type capable of delivering beams from various directions to the isocenter are called isocentric gantries.

The gantry beam delivery system comprises devices for shaping the beam to match the target. There are two major techniques used in particle beam therapy to shape the beam: the more common passive scattering techniques and the more advanced dynamic radiation techniques. An example of a dynamic radiation technique is the so-called pencil beam scanning (PBS) technique. In PBS a narrow pencil beam is magnetically scanned across a plane orthogonal to the central beam axis. Lateral conformity in the target volume is obtained by adequate control of the scanning magnets. Depth conformity in the target volume is obtained by adequate control of the beam energy. In this way, a particle radiation dose can be delivered to the entire 3D target volume.

The particle beam energies required to have sufficient penetration depth in the patient depend on the type of particles used. For example, for proton therapy, proton beam energies are typically ranging between 70 MeV and 250 MeV.

For each required penetration depth the beam energy needs to be varied. The energy spread of the beam should be limited as this directly influences the so-called distal dose fall-off.

However, not all accelerator types can vary the energy. For fixed energy accelerators (e.g. a fixed isochronous cyclotron) typically an energy selection system (ESS) is installed between the exit of the accelerator and the treatment room as shown in FIGS. 1, 2 and 3. Such an energy selection system is described by Jongen et al. in "The proton therapy system for the NPTC: equipment description and progress report", Nuc. Instr. Meth. In Phys. Res. B 113 (1996) 522-525. The function of the Energy Selection System (ESS) is to transform the fixed energy beam extracted from the cyclotron (e.g. 230 MeV or 250 MeV for protons) into a beam having an energy variable between the cyclotron fixed energy down to a required minimum energy (for example 70 MeV for protons). The resulting beam must have a verified and controlled absolute energy, energy spread and emittance.

The first element of the ESS is a carbon energy degrader which allows to degrade the energy by putting carbon elements of a given thickness across the beam line. Such an energy degrader is described in patent EP1145605. As a result of this energy degradation, there is an increase in emittance and energy spread of the beam. The degrader is followed by emittance slits to limit the beam emittance and by a momentum or energy analysing and selection device to restore (i.e. to limit) the energy spread in the beam.

A layout of such a known energy selection system 10 is shown in FIG. 1 together with a stationary, fixed energy accelerator 40 (in this example a cyclotron). After the degrader and emittance limiting slits, the beam passes through a 120° achromatic bend made up of two groups of two 30° bends. To meet the specification for the distal fall off, the momentum spread or the energy spread in the beam is limited by a slit placed at the center of the bend. The beam is focused by quadrupoles before the bend and between the two groups of two 30° bending magnets so that the emittance width of the beam is small and the dispersion is large at the position of the slit.

The entire beam line starting at the energy degrader 41 up to the treatment isocenter 50 forms an optical system that is achromatic, i.e. a beam-optical system which has imaging properties independent from momentum (dispersionless) and independent from its transverse position. The beam line can be divided in multiple sections and each section is forming itself an achromat. As shown in FIG. 2, the first section is the ESS 10 followed by an achromatic beamline section that brings the beam up to the entrance point of a treatment room. In the case of a gantry treatment room, this entrance point is the entrance point or coupling point of the rotating gantry 15. The gantry beam line is then forming a third achromatic beam line section. In the case of a single treatment room particle therapy configuration, as shown in FIG. 3, the beam line comprises two achromatic beam line sections: a first section is the ESS 10 that brings the beam up to the gantry entrance point and the second achromatic section corresponds to the rotating gantry 15 beam line. At the gantry entrance point, the beam must have the same emittance in X and Y in order to have a gantry beam optics solution that is independent from the gantry rotation angle. The X and Y axis are perpendicular to each other and to the central beam trajectory. The X axis is in the bending plane of the dipole magnets.

A disadvantage of the use of such a degrader and energy analyzer is that this device requires a relative large space area as shown in FIG. 1 and hence a large building footprint is required. The installation of an ESS results also in an extra equipment cost.

The present invention aims to provide a solution to overcome at least partially the problems of the prior art. It is an objective of the present invention to provide a charged particle therapy apparatus that has a reduced size and that can be built at a reduced cost when compared to the prior art particle therapy apparatus.

SUMMARY OF THE INVENTION

The present invention is set forth and characterized by the appended claims.

In the prior art particle therapy configurations as shown for example in FIGS. 1 to 3, the functionalities of limiting the momentum spread (or energy spread, which is equivalent) and the emittance of the beam is performed by a separate device, namely with the energy selection system (ESS) 10, which is installed between the stationary accelerator 40 and the rotating gantry 15,. As shown on FIG. 1, a first element of the ESS is an energy degrader 41 which is used to degrade the energy of the particle beam of the fixed-energy accelerator 40.

With the present invention, a rotatable gantry beam delivery system is provided having a gantry beam line configuration which fulfils multiple functions:
- The known function of transporting, bending and shaping an entering particle beam in such a way that a particle treatment beam can be delivered at a gantry treatment isocenter for use in particle therapy;
- The additional function of limiting the energy spread of the entering particle beam to a selected maximum value.

With the present invention, the ESS functionality of limiting the energy spread or momentum spread of the beam to a selected value is performed by the gantry system itself. Hence the size and cost of a particle therapy facility can be reduced. In the context of the present invention, the momentum spread is defined as the standard deviation of the momentums of the particles at a given location and is expressed as a percentage of the average momentum of all particles at this location. Whatever the location of the means for limiting the momentum spread in the gantry, these means are preferably designed for limiting said momentum spread to 10%, more preferably to 5%, and even more preferably to 1% of the average momentum of all particles.

Preferably, the gantry also fulfils a second additional function of limiting the transverse beam emittance of the entering particle beam to a selected maximum value, which further reduces cost and size of the particle therapy facility.

More preferably, the gantry according to the invention also comprises a collimator installed in-between the gantry entrance point and a first quadrupole magnet in the gantry. This collimator is used for reducing the emittance of the beam before the beam is arriving at the first magnet in the gantry beam line.

In an alternative preferred embodiment, the above mentioned collimator is installed outside of the gantry, i.e. in-between the energy degrader and the entrance point of the gantry.

According to the invention, a particle therapy apparatus is also provided comprising a stationary particle accelerator, an energy degrader and a rotatable gantry having means to limit the momentum spread of the beam. Preferably said gantry also comprises means to limit the emittance of the beam.

Alternatively, a particle therapy apparatus is provided comprising a stationary particle accelerator, an energy degrader, a rotatable gantry comprising means to limit the momentum spread of the beam and a collimator installed in-between said energy degrader and said gantry for limiting the emittance of the beam.

More preferably, said gantry comprises additional means to limit the emittance of the beam.

DETAILED DESCRIPTION OF PREFERRED EMBODIMENTS

Figure 1:
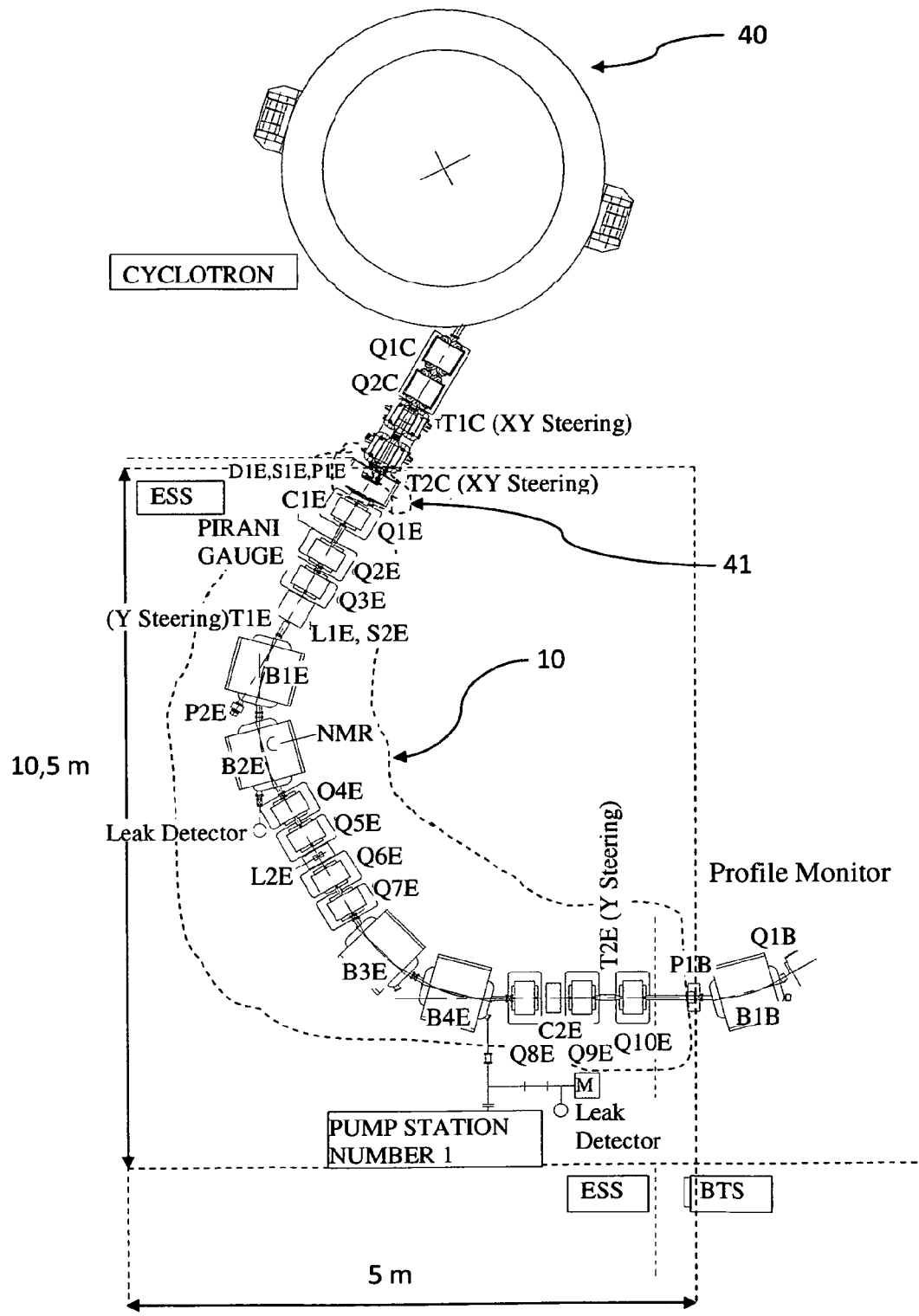
FIG. 1 shows a representation of a known energy selection system for use with a fixed energy cyclotron

The present invention will now be described in detail in relation to the appended drawings. However, it is evident that a person skilled in the art may conceive several equivalent embodiments or other ways of executing the present invention. The drawings described are only schematic and are non-limiting. In the drawings, the size of some of the elements may be exaggerated and not drawn on scale for illustrative purposes.

Figure 3:
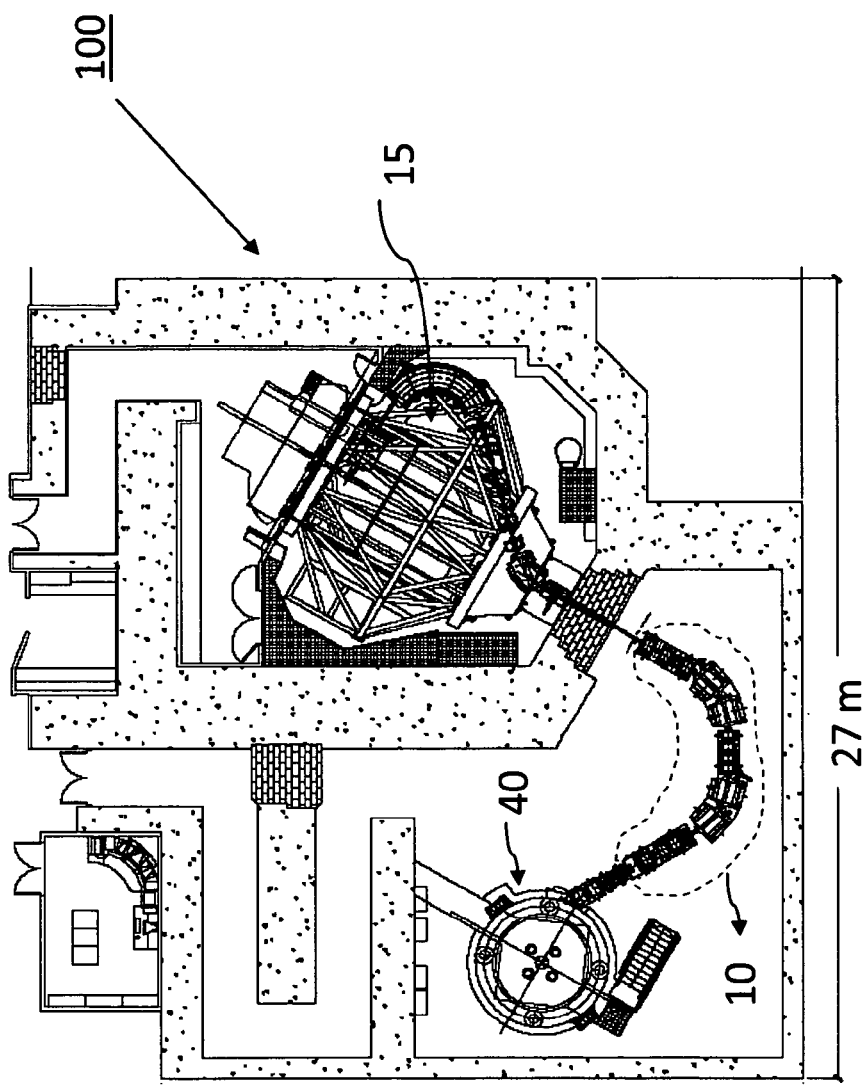
FIG. 3 shows a schematic representation of a known layout of a single room particle therapy configuration
Figure 4:
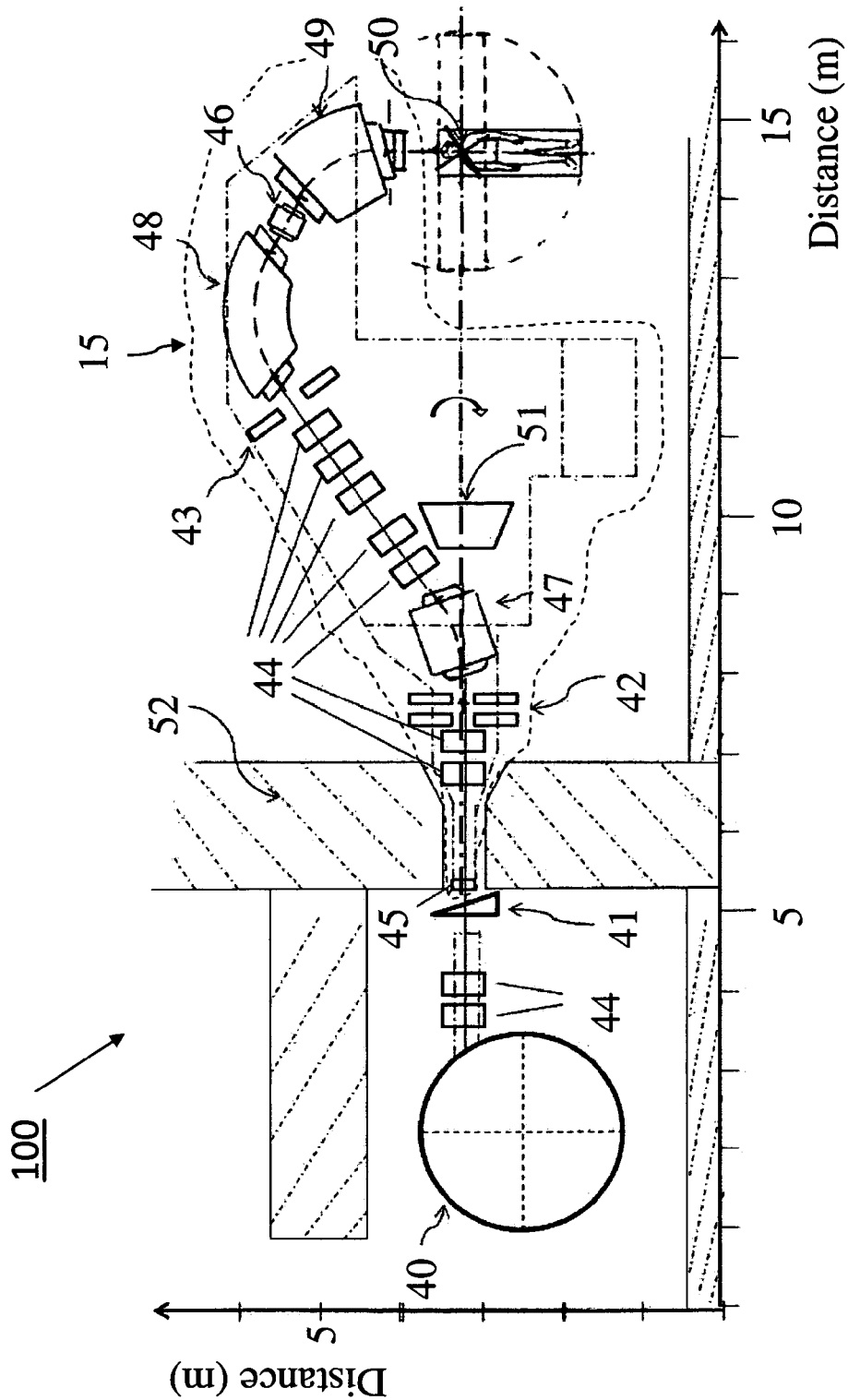
FIG. 4 shows schematically an exemplary embodiment of a device according to the invention.

A exemplary particle therapy configuration according to the invention is shown in FIG. 4. In this example, the rotatable gantry according to the invention is coupled with a stationary-, fixed energy-particle accelerator 40 to form a single room particle therapy apparatus 100. An example of a particle accelerator for protons is a superconducting synchrocyclotron which has a compact geometry (e.g. with an extraction radius of 1.2 m). The gantry according to the invention is installed in the gantry room and a shielding wall (e.g. a 1.7 m thick concrete wall) separates the gantry room from the accelerator room. An energy degrader 41 is installed between the accelerator 40 and a gantry entrance point 45 (coupling point). This energy degrader 41 is positioned within the accelerator room just in front of the shielding wall 52 separating the accelerator room from the gantry room. The gantry entrance point 45 is located after the degrader 41 and is an entrance window for the beam line of the gantry. This entrance window 45 is the first part of a gantry beam line section where the beam is entering the gantry in a direction substantially along the rotation axis of the gantry. The rotation axis of the gantry is indicated by a horizontal dash-dotted line passing through the isocentrer 50 and the entrance point 45. As shown in FIG. 4, there is no momentum or energy analyser device installed between the degrader and the gantry entrance point as is the case in the prior art systems (FIGS. 1 to 3).

Figure 2:
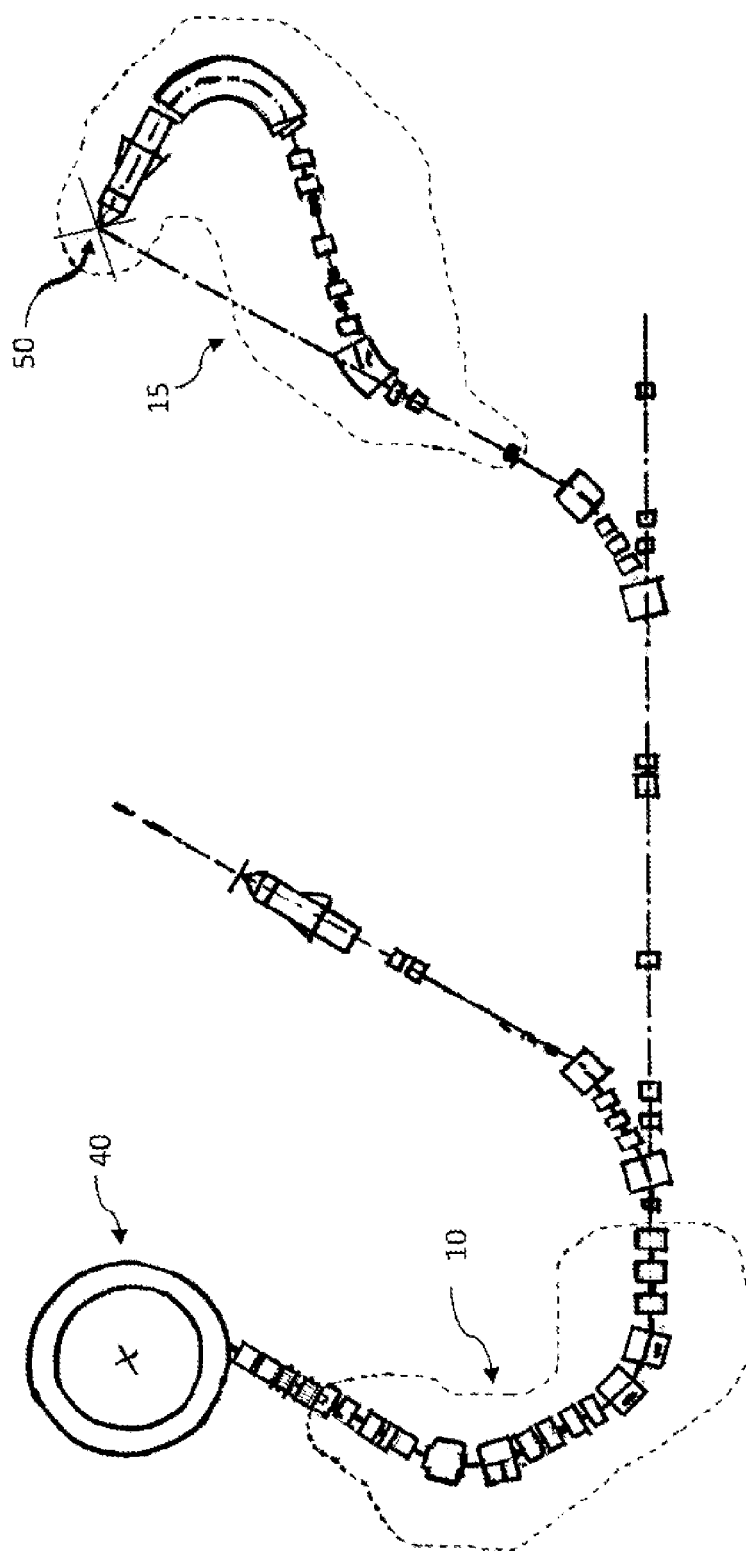
FIG. 2 shows a typical layout of a known particle therapy beam line configuration

Similar as in the prior art configurations shown in FIGS. 1 to 3, there is a short beam line section between the exit of the accelerator and the degrader 41, where for example two quadrupole magnets 44 are installed for transporting and focussing the beam into a small spot (for example between 0.5 mm and 2 mm one sigma) at the energy degrader. The energy degrader 41 is for example a rapidly adjustable, servo controlled, rotating, variable thickness, cylinder of degrading material (as disclosed in EP1145605). The distance between the exit of the accelerator and the degrader can be about 2 m. Other types of energy degrading systems, e.g. lateral moving wedge shaped based degraders can be used as well.

The energy degrader currently used by the applicant has at its entrance an integrated horizontal-vertical beam profile monitor which allows measurement of the size and position of the beam spot and, through a control system algorithm, means for automatic tuning of the up-stream beam optics. Hence, the beam at the degrader 41 can be well defined, for example, the beam is focused into a small waist with a half width not exceeding 2 mm in both planes. With these input beam conditions, the output emittance of the beam degraded in energy is dominated by multiple scattering in the degrader and is relatively independent from the input conditions. The resulting beam after energy degradation can be considered as a diverging beam from a virtual waist in X and Y at the degrader with a given size and divergence. The two orthogonal coordinate axis X and Y are perpendicular (transverse) to the central beam trajectory. The emittances in X and Y (also called "transverse emittances") can be considered to be substantially identical at this point. The larger the energy reduction introduced by the degrader, the larger will be the transversal emittance in X and Y and the larger will be the momentum spread of the degraded beam.

The embodiment of the invention is a gantry configuration comprising means 43 to limit the momentum spread of the incoming beam. A beam entering the gantry comprising particles having an average momentum value and a momentum spread.

To limit the momentum spread of the incoming beam, a pair of momentum analyzing slits 43 are installed in the gantry.

These momentum analyzing slits 43 are preferably located at a position along the beam path where the particles of the beam are dispersed according to their momentum.

More preferably, these slits are installed at a position where the nominal dispersion is larger than the nominal beam size. The nominal dispersion is defined as a transversal displacement of a particle whose momentum differs by 1% (one percent) of an average momentum P of all particles of the beam. The nominal beam size is defined as the one sigma beam size value in X of a mono-energetic particle beam having the average momentum P. Suppose that the nominal dispersion is 2.5 cm: this means that a particle having a momentum $P'=1.01.P$ will be displaced by 2.5 cm in X from a particle having momentum P. In this example, a particle having a momentum $P'=0.99.P$ will also be displaced in X by 2.5 cm but having an X coordinate with an opposite sign.

The momentum limiting slits can for example be installed at a position where the nominal beam size in X is between 0.2 cm and 1 cm and the nominal dispersion in X is between 1 cm and 3 cm. By opening or closing the slits, the maximum momentum spread that is required (selected) can be obtained. One can for example select to limit the maximum momentum spread to 0.5% of the average momentum by adjusting the slits correspondingly. If one wants to limit the maximum momentum spread to 0.4% of the average momentum, then one has to close the pair of momentum slits more. For this purpose a calibration curve can be established, defining the slit opening as function of the required momentum spread.

In the configuration of FIG. 4, the nominal dispersion is large in comparison with the beam size at a position in-between gantry quadrupole magnet number seven and the second dipole magnet 48 and hence this is a preferred position to install the momentum spread limiting slits. These slits can for example be installed just before the second dipole magnet 48. The exact position can vary depending on the detailed gantry configuration.

Instead of using a pair of slits as means for reducing the momentum spread of the beam, other means can be used as well. For example one can use apertures or collimators with various diameters which can be put in the beam line, preferably at the above discussed positions.

In the example shown in FIG. 4, a gantry for delivering scanning beams at the treatment isocenter 50 is presented and the beam line of this gantry comprises three dipole magnets 47,48,49 and seven quadrupole magnets 44. In this gantry configuration, scanning magnets 46 are installed upstream of the last dipole magnet 49. Between the gantry entrance point 45 and the first dipole magnet and in between the first and second dipole magnet there are respectively, two and five quadrupole magnets.

Preferably, in addition to the means 43 to limit the momentum spread of the beam, also means 42 to limit the transverse beam emittance can be installed in the gantry 15. For this purpose, two pairs of slits (in X and Y) limiting the beam divergence can for example be installed in-between the second quadrupole magnet and the first dipole magnet 47. Hence, by limiting the divergence of the beam, the transverse beam emittance, which is proportional to the beam divergence, is limited. The first two quadrupoles installed in the gantry in-between the entrance point 45 and the first dipole magnet 47 serve to focus the divergent beam, originating from the degrader, before the beam reaches the divergence limiting slits. To what extent the beam emittance needs to be reduced will depend on what the maximum emittance the gantry can accept to efficiently transport the beam and it will also depend on what the beam requirements are at the treatment isocenter (such as for example the beam size required at the treatment isocenter). Acceptable beam emittances and beam sizes may depend on the technique used for shaping the beam (e.g. pencil beam scanning or passive scattering). The example given in FIG. 4 is for a scanning beam delivery system. For a pencil beam proton scanning system the beam emittance can for example be limited to 7.5 Pi mm mrad in both X and Y. For practical beam tuning purposes, just in front, downstream, of the divergence limiting or emittance limiting slits, a beam profile monitor can be installed (not shown on FIG. 4). Instead of using a pair of slits in X and Y as means for reducing the divergence of the beam, other means can be used as well. For example one can use apertures or collimators with various diameters which can be put in the beam line.

If the energy reduction of the beam is very large (e.g. reduction of 250 MeV protons down to 70 MeV), the emittance and divergence of the beam becomes very large and the diameter of the beam, just before the first quadrupole magnet in the gantry, can become larger than the diameter of the beam line pipe. For this purpose a collimator (not shown in FIG. 4) can furthermore be installed upstream of the first quadrupole magnet in the gantry 15 to cut off already a part of the beam. This collimator can be installed in the gantry 15 in-between the entrance point 45 and the first quadrupole magnet of the gantry. Alternatively, such a collimator can be installed outside the gantry, i.e. in-between the degrader and the entrance point 45 of the gantry 15. When such a collimator for limiting the emittance of the beam is installed in either of the two positions mentioned above, in an alternative gantry embodiment the means 42 for limiting the emittance can be omitted.

When a particle beam hits divergence and/or momentum limiting slits, neutrons are produced. To limit the neutron radiation at the level of the treatment isocenter 50 where the patient is positioned, adequate shielding need to be provided. As neutrons are mainly emitted in the direction of the beam, one can install just after the first dipole magnet, across the axis of rotation of the gantry, a neutron shielding plug 51 to shield the neutrons produced on means to limit the emittance of the beam installed upstream of the first dipole magnet 47. As the neutrons are mainly emitted in the direction of the beam, neutrons produced at the momentum limiting slits 43 are not directing to the patient. Nevertheless, a local neutron shielding (not shown on FIG. 4) can be installed around the momentum limiting slits 43 in order to reduce overall neutron background radiation.

In order not to overload FIG. 4, details of the mechanical construction of the gantry have been omitted on purpose. Examples of such mechanical elements not shown on FIG. 4 are: two spherical roller bearings for rotating the gantry by at least 180° around the patient, a gantry drive and braking system, a drum structure for supporting a cable spool, a counterweight needed to get the gantry balanced in rotation, . . .

When designing a gantry for particle therapy, several beam optical conditions need to be fulfilled. At the gantry entrance point 45 the beam must have identical emittance parameters in X and Y in order to have a gantry beam optics solution that is independent from the gantry rotation angle. As discussed above, these conditions are naturally fulfilled when placing the energy degrader just in front of the gantry entrance point. In addition, the following beam optical conditions need to be met:
1. The gantry beam-optical system must be double achromatic, i.e. the beam imaging properties must be independent from momentum (dispersionless) and independent from position.
2. The maximum size of the beam (one sigma) inside the quadrupoles should preferably not exceed 2 cm in order to keep a reasonable transmission efficiency in the gantry.

There is also a third condition that however can vary depending on the technique used for shaping the beam as discussed above. For a scanning system this third condition can be described as follows:
3. At the isocenter 50 the beam must have a small waist, of substantially identical size in X and Y.

For a scattering system, required beam sizes can be specified more upstream of the isocenter (for example at the exit of the last bending magnet) and the acceptable beam sizes for scattering are in general larger than for scanning (for example 1 cm at the exit of the last bending magnet)

In addition to these three conditions (1 to 3), new requirements are introduced resulting from the current invention:
4. At the position of the energy spread limiting slits 43, the nominal dispersion in X should preferably be large in comparison with the nominal beam size in X (for examples of values see discussion above).

Preferably, a gantry according to the invention also comprises means to limit the emittance of the beam. This results in an additional requirement:
5. At the position of the emittance limiting slits 42, the beam must have beam optical parameters (size and divergence) in X and Y that allow to cut the divergence. This means for example that the beam must have a reasonable size (e.g. 0.5 cm to 2 cm, one sigma).

Figure 5:
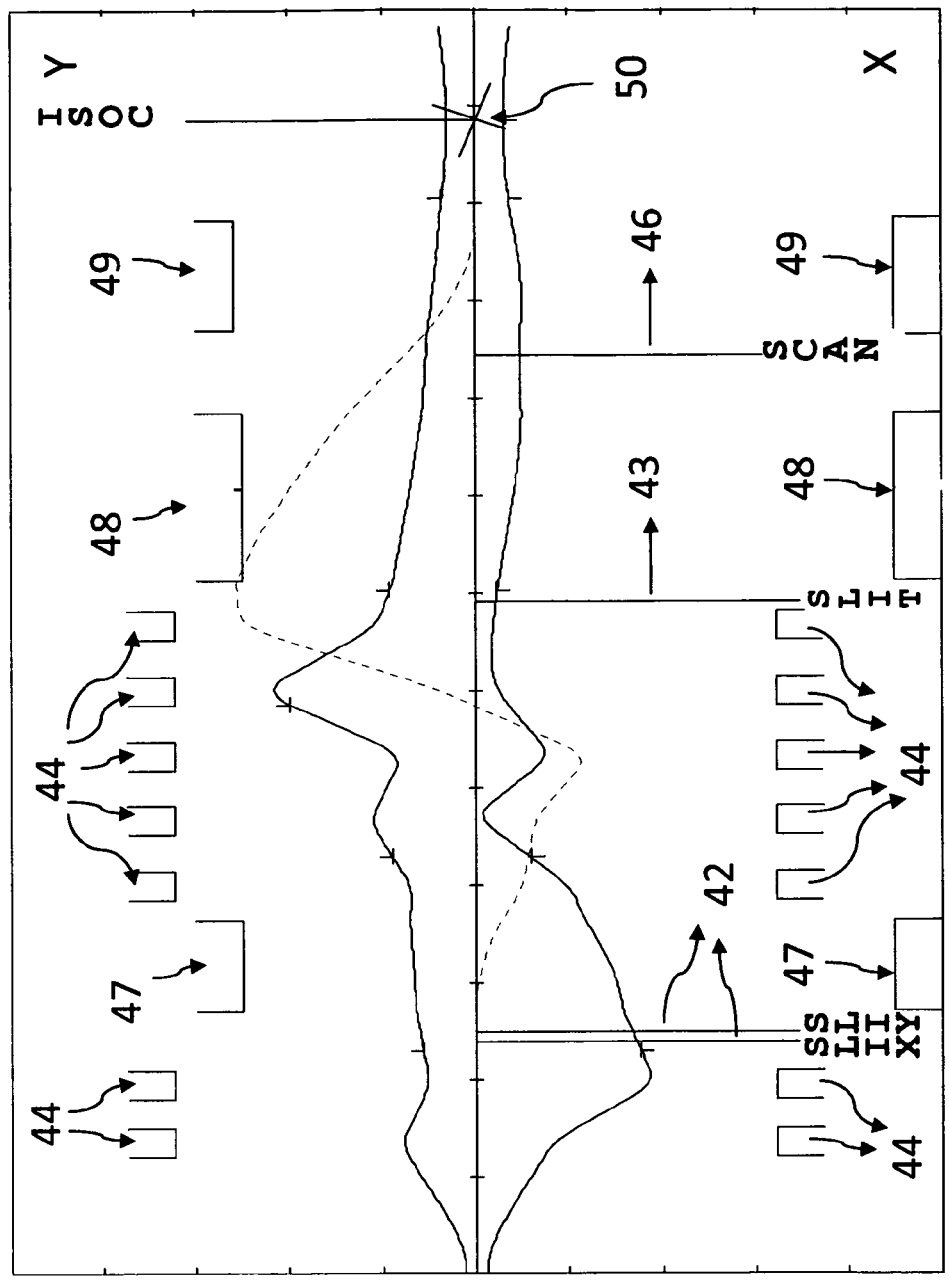
FIG. 5 shows results of beam optics calculation for an exemplary gantry according to the invention.

The gantry configuration shown in FIG. 4 is based on a beam optical study performed with the beam optics "TRANSPORT" code (PSI Graphic Transport Framework by U. Rohrer based on a CERN-SLAC-FERMILAB version by K. L. Brown et al.). The beam envelopes in X and Y in the gantry beam line for an entering proton beam of 170 MeV are shown in FIG. 5 as an example. The beam envelopes are plotted for the X direction and Y direction in the lower panel and upper panel, respectively. In this example the emittance of the final beam is 12.5 Pi mm mrad. This corresponds to a situation where the divergence of the incoming beam has been limited to 6 mrad in X and Y. The beam transported through the system can then be considered as a beam starting at the degrader with a small beam spot of 1.25 mm and a divergence of 6 mrad. With this beam optics a beam size at the treatment isocenter of 3.2 mm (one sigma value) is obtained which is an adequate value for performing pencil beam scanning. The positions of the quadrupole magnets and dipole magnets are shown on FIG. 5. The transversal positions of the dipole magnets (the vertical gaps) are not shown on scale in this figure and the purpose is only to indicate their position along the central trajectory. Especially the gap in X an Y of the last bending magnet 49 are much larger than on the scale of FIG. 5 as a large opening is needed because the scanning magnets are positioned upstream of this dipole magnet and a large scanning area need to be covered at isocenter. The position of the scanning magnets along the beam path is indicated by a vertical line. The dotted line represents the nominal dispersion in X of the beam. As shown, just before the second dipole magnet 48 a large nominal dispersion value is obtained and this is the position where the momentum limiting slits 43 are preferably installed. The position along the central beam trajectory of the momentum limiting slits 43 is indicated by a vertical line on FIG. 5. The nominal beam size in X at the momentum limiting slits is about 0.23 cm while the nominal dispersion in X at this position is about 2.56 cm, hence obtaining a good momentum separation of the incoming beam.

Preferably, also divergence limiting slits 42 are used. A good position for these slits 42 is indicated on FIG. 5 by a vertical line. At this position, the beam size in X and Y is about 1.8 cm and 0.6 cm, respectively. This beam optical solution presented fulfils the conditions of a double achromat.

In the example shown in FIG. 4 and FIG. 5, a three dipole gantry configuration was used with dipole bending angles of respectively 36°, 66° and 60°. However, the invention is not limited to a specific gantry configuration for what concerns number of dipoles or bending angles of the dipoles. The invention is neither limited to the number of quadrupole magnets and the relative positions of the quadrupoles with respect to the dipole magnets.

As a second example, the invention has been applied to a conical two dipole large throw gantry. This corresponds to the gantry configuration shown on FIG. 2 and FIG. 3. These large throw gantries have been built by the applicant and are discussed by Pavlovic in "Beam-optics study of the gantry beam delivery system for light-ion cancer therapy", Nucl. Instr. Meth. In Phys. Res. A 399(1997) on page 440. In these gantries a first 45° dipole magnet bends the beam away from the axis of rotation of the gantry and the beam then further follows a second straight beam line section before entering the second 135° dipole magnet which is bending and directing the beam essentially perpendicular to the axis of rotation. The straight beam line section between the gantry entrance point and the first 45° dipole magnet comprises, in the original gantry design, four quadrupole magnets (FIG. 2 is a configuration having only two quadrupole magnets installed in this beam line section), and the second straight section between the first and second dipole magnet comprises five quadrupole magnets. With this gantry the distance between the exit of the last bending magnet and the treatment isocenter is 3 m and the beam shaping elements configured in a so-called nozzle are installed upstream of the last bending magnet. This nozzle uses either the passive scattering technique or the scanning technique for shaping the beam conform the treatment target. The scanning magnets are part of the nozzle and are hence installed downstream of the last gantry dipole magnet.

Figure 6:
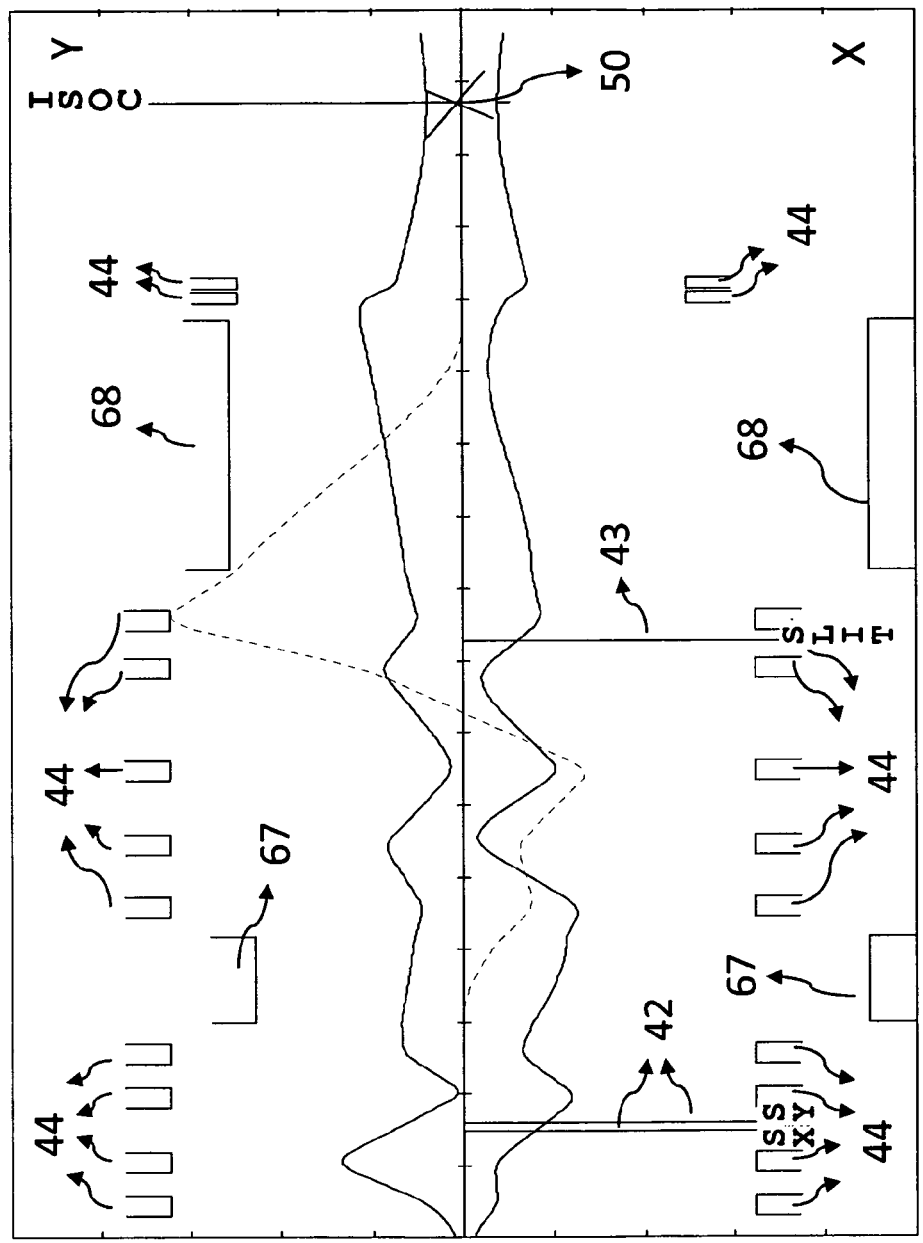
FIG. 6 shows results of beam optics calculation for another exemplary gantry configuration according to the invention.

A beam optical analysis has been performed for this two dipole gantry configuration. The same conditions and requirements as discussed above have been respected. The resulting beam envelopes in this gantry are shown in FIG. 6 for a proton beam of 160 MeV. The beam envelopes are plotted for the X direction and Y direction in the lower panel and upper panel, respectively. The positions along the central beam path of the 45° dipole magnet 67, the 135° dipole magnet 68 and the various quadrupole magnets 44 are indicated in FIG. 6. Also here the energy degrader is installed just before the entrance window of the gantry and, as an example, in this calculation the divergence was cut at 8 mrad and the emittance of the final beam is 10 Pi mm mrad both in X and Y.

The beam envelope as shown in FIG. 6 starts at the gantry entrance window and the beam has a size of 1.25 mm (one sigma value). In this gantry configuration the first straight section between the entrance window and the first 45° gantry bending magnet 67, comprises four quadrupole magnets 44. Divergence limiting devices 42 are installed in between the second and third quadruople magnet and are indicated by a vertical line on FIG. 6. The momentum spread limiting slits 43 are installed at a position where the nominal dispersion in X is large compared to the nominal beam size. The dotted line on FIG. 6 represents the nominal dispersion in X of the beam. The position of the momentum spread limiting slits 43 are indicated by a vertical line on FIG. 6. At this position the nominal dispersion is about 2.6 cm in X and the nominal beam size in X (one sigma value) is about 0.6 cm which is adequate for analysing the incoming beam according to momentum and limiting the momentum spread to a given value by setting the slits at the corresponding position. The beam envelope shown in FIG. 6 is a tuning solution for a nozzle using the scanning technique (the scanning magnets are installed downstream of the 135° dipole magnet but are not shown on FIG. 6). This gantry configuration used in this beam optics study also comprises two quadrupole magnets installed upstream of the 135° last dipole magnet 68 as indicated on FIG. 6. With this tuning solution, a double waist in X and Y is obtained at isocenter having a beam size of 4 mm (one sigma value), which is suitable for performing pencil beam scanning. This beam optical solution fulfils the conditions of a double achromat.

A particle therapy apparatus 100 can be formed by combining a stationary, fixed energy particle accelerator, an energy degrader and a rotatable gantry according to the invention, i.e. a rotatable gantry comprising means for limiting the energy spread or momentum spread of the beam and preferably also comprising means for limiting the emittance of the beam. As shown on FIG. 4, which is an example of a proton therapy apparatus, a compact geometry can be obtained and the building footprint that is needed to install this apparatus is smaller than with a separate energy selection system.

Although the embodiments described are focussing on proton gantries, the invention is not limited to proton gantries. The person skilled in the art can easily apply the elements of the invention, i.e. means for analyzing the beam (limiting the emittance and limiting the energy spread), to gantries for use with any type of charged particles such as e.g. a gantry for carbon ions or other light ions.

Gantries for particle therapy have been designed since many years and, in combination with stationary, fixed energy particle accelerators, a separate energy selection system was always installed in the beam line between the accelerator and the gantry. According to the present invention a new gantry configuration is provided comprising means for limiting the energy spread or momentum spread of the beam and preferably also comprising means for limiting the emittance of the beam. Hence the gantry itself comprises functionalities of the standard prior art energy selection system. By designing a gantry with these means to analyse the beam as described, a more compact particle therapy apparatus can be built.

The invention claimed is:

1. A particle therapy apparatus comprising:
   a particle beam generator configured to output a particle beam having a predetermined energy;
   an energy degrader for reducing an energy of the predetermined-energy particle beam, the energy degrader configured to output a degraded particle beam having an energy spread that is increased with respect to an energy spread of the predetermined-energy particle beam; and
   a rotatable gantry including:
     an entrance point configured to receive the degraded particle beam in a direction substantially along a rotation axis of the gantry;
     a beam optic system having a plurality of dipole magnets, including a first dipole magnet and a last dipole magnet, and configured for beam transport along a beam path to a target, wherein the beam optic system is configured to have a first position along the beam path where a nominal dispersion at the first position is larger than a nominal beam size at the first position;
     an adjustable spread-limiting device, installed at the first position, having a spacing to limit an energy spread of the degraded particle beam and configured to output a limited beam having an energy spread that is decreased with respect to the energy spread of the degraded particle beam,
   wherein the spacing of the adjustable spread-limiting device is configured to be adjusted to a selected beam opening based on a selected value reflecting a maximum energy spread for the limited beam to be output by the adjustable spread-limiting device, and
   wherein the adjustable spread-limiting device is installed downstream of the first dipole magnet and upstream of the last dipole magnet of the plurality of dipole magnets, and there is no energy analyzer between the energy degrader and the gantry entrance point.

2. The particle therapy apparatus according to claim 1, wherein the particle beam generator is a cyclotron.

3. The particle therapy apparatus according to claim 1, wherein the adjustable spread-limiting device is located at the first position, wherein the nominal dispersion being defined as a transversal displacement of a particle whose momentum differs by 1% (one percent) of an average momentum P of all particles of the beam, the nominal beam size being defined as a one sigma beam size value of a mono-energetic particle beam having the average momentum P.

4. The particle therapy apparatus according to claim 1, wherein the rotatable gantry further comprises at least one emittance slit, emittance aperture, or emittance collimator configured to limit a transverse emittance of the particle beam to a selected maximum value.

5. The particle therapy apparatus according to claim 4, wherein the at least one emittance slit, or emittance aperture, or emittance collimator is located upstream of the adjustable spread-limiting device.

6. The particle therapy apparatus according to claim 1, wherein the spacing of the adjustable spread-limiting device is configured to be adjusted to a selected beam opening based on a predefined calibration curve that defines beam opening as a function of required energy spread.

7. The particle therapy apparatus according to claim 1, wherein the adjustable spread-limiting device has at least one aperture configured to be opened or closed in response to the selected value reflecting the target energy spread, wherein the opening or closing of the at least one aperture causes an adjustment of the spacing of the adjustable spread-limiting device.

8. The particle therapy apparatus according to claim 1, wherein the adjustable spread-limiting device includes at least one opening.

9. The particle therapy apparatus according to claim 1, wherein the adjustable spread-limiting device includes at least one spread-limiting aperture.

10. The particle therapy apparatus according to claim 1, wherein the adjustable spread-limiting device includes a collimator.

11. The particle therapy apparatus according to claim 1, wherein a distance between an output of the particle beam generator and the entry point of the rotatable gantry is less than three meters.

12. The particle therapy apparatus according to claim 1, wherein a distance between an output of the particle beam generator and the degrader is about two meters.

13. The particle therapy apparatus according to claim 4, wherein the at least one emittance slit, emittance aperture, or emittance collimator is further configured to limit a transverse emittance of the particle beam to a selected maximum value of horizontal transverse emittance and vertical transverse emittance.

14. The particle therapy apparatus according to claim 1, wherein the first dipole magnet is a 45 degree bending dipole magnet and the last dipole magnet is a 135 degree bending dipole magnet.

15. The particle therapy apparatus according to claim 1, wherein
the first dipole magnet is a 36-degree dipole magnet and the last dipole magnet is a 60-degree bending dipole magnet, and
the plurality of dipole magnets further comprises a third 66-degree bending dipole magnet located between the first dipole magnet and the last dipole magnet.

16. The particle therapy apparatus according to claim 1, wherein the energy degrader reduces the energy of the predetermined-energy particle beam by more than two-thirds.

17. The particle therapy apparatus according to claim 3, wherein the rotatable gantry further includes at least one emittance slit, emittance aperture, or emittance collimator configured to limit a transverse emittance of the particle beam to a selected maximum value and located upstream of the adjustable spread-limiting device.

18. The particle therapy apparatus according to claim 17, wherein the spacing of the adjustable spread-limiting device is configured to be adjusted to a selected beam opening based on a predefined calibration curve that defines beam opening as a function of required energy spread.

19. The particle therapy apparatus according to claim 18, wherein a distance between an output of the particle beam generator and the degrader is about two meters.

* * * * *